US008425548B2

(12) United States Patent  (10) Patent No.: US 8,425,548 B2
Connor  (45) Date of Patent: Apr. 23, 2013

(54) OCCLUDING MEMBER EXPANSION AND THEN STENT EXPANSION FOR ANEURYSM TREATMENT

(75) Inventor: Robert A. Connor, Minneapolis, MN (US)

(73) Assignee: Aneaclose LLC, Forest Lake, MN (US)

( * ) Notice: Subject to any disclaimer, the term of this patent is extended or adjusted under 35 U.S.C. 154(b) by 203 days.

(21) Appl. No.: 13/134,792

(22) Filed: Jun. 17, 2011

(65) Prior Publication Data

US 2012/0004682 A1  Jan. 5, 2012

Related U.S. Application Data

(60) Provisional application No. 61/398,918, filed on Jul. 1, 2010.

(51) Int. Cl.
*A61M 29/00* (2006.01)
(52) U.S. Cl.
USPC ............ 606/194; 623/1.15; 623/1.11
(58) Field of Classification Search .......... 606/194, 606/151, 198; 623/1.11, 1.12, 1.17, 1.15, 623/1.18, 1.23; 604/264
See application file for complete search history.

(56) References Cited

U.S. PATENT DOCUMENTS

| | | | |
|---|---|---|---|
| 5,334,210 A | 8/1994 | Gianturco | |
| 5,382,259 A | 1/1995 | Phelps et al. | |
| 5,522,822 A | 6/1996 | Phelps et al. | |
| 5,645,559 A | 7/1997 | Hachtman et al. | |
| 5,690,666 A | 11/1997 | Berenstein et al. | |
| 5,718,711 A | 2/1998 | Berenstein et al. | |
| 5,723,004 A | 3/1998 | Dereume et al. | |
| 5,749,894 A | 5/1998 | Engelson | |
| 5,766,219 A | 6/1998 | Horton | |
| 5,769,882 A | 6/1998 | Fogarty et al. | |
| 5,769,884 A | 6/1998 | Solovay | |
| 5,861,003 A | 1/1999 | Latson et al. | |
| 5,916,235 A | 6/1999 | Guglielmi | |
| 5,928,260 A | 7/1999 | Chin et al. | |
| 5,941,249 A | 8/1999 | Maynard | |
| 5,948,018 A | 9/1999 | Dereume et al. | |
| 5,951,599 A | 9/1999 | McCrory | |
| 5,976,162 A | 11/1999 | Doan et al. | |
| 6,024,754 A | 2/2000 | Engelson | |
| 6,063,111 A | 5/2000 | Hieshima et al. | |
| 6,096,034 A | 8/2000 | Kupiecki et al. | |
| 6,165,193 A | 12/2000 | Greene, Jr. et al. | |
| 6,165,212 A | 12/2000 | Dereume et al. | |
| 6,168,592 B1 | 1/2001 | Kupiecki et al. | |
| 6,270,523 B1 | 8/2001 | Herweck et al. | |
| 6,299,619 B1 | 10/2001 | Greene, Jr. et al. | |
| 6,309,367 B1 | 10/2001 | Boock | |

(Continued)

*Primary Examiner* — Ryan Severson
*Assistant Examiner* — Tin Nguyen

(57) ABSTRACT

This invention is a device and method to occlude an aneurysm comprising: a laterally-expanding occluding member (such as a relatively-flat balloon, mesh, net, or patch) that is positioned within the parent vessel of the aneurysm and then expanded laterally; and a radially-expanding structural member (such as a stent) that is positioned within the parent vessel of the aneurysm and then expanded radially after, or concurrently with, expansion of the laterally-expanding occluding member. Expansion of the radially-expanding member presses and holds the laterally-expanding occluding member into contact with the aneurysm neck, so that the laterally-expanding occluding member at least partially covers the aneurysm neck and reduces blood flow to the aneurysm. This invention has several potential advantages over devices and methods in the prior art, especially for treatment of wide-neck and fusiform aneurysms.

19 Claims, 2 Drawing Sheets

U.S. PATENT DOCUMENTS

| | | |
|---|---|---|
| 6,309,413 B1 | 10/2001 | Dereume et al. |
| 6,331,191 B1 | 12/2001 | Chobotov |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,375,668 B1 | 4/2002 | Gifford et al. |
| 6,391,037 B1 | 5/2002 | Greenhalgh |
| 6,409,749 B1 | 6/2002 | Maynard |
| 6,428,558 B1 | 8/2002 | Jones et al. |
| 6,454,780 B1 | 9/2002 | Wallace |
| 6,500,190 B2 | 12/2002 | Greene, Jr. et al. |
| 6,506,204 B2 | 1/2003 | Mazzocchi |
| 6,547,804 B2 | 4/2003 | Porter et al. |
| 6,569,190 B2 | 5/2003 | Whalen et al. |
| 6,585,748 B1 | 7/2003 | Jeffree |
| 6,602,261 B2 | 8/2003 | Greene, Jr. et al. |
| 6,605,111 B2 | 8/2003 | Bose et al. |
| 6,613,074 B1 | 9/2003 | Mitelberg et al. |
| 6,626,928 B1 | 9/2003 | Raymond et al. |
| 6,656,214 B1 | 12/2003 | Fogarty et al. |
| 6,673,103 B1 | 1/2004 | Golds et al. |
| 6,723,108 B1 | 4/2004 | Jones et al. |
| 6,746,468 B1 | 6/2004 | Sepetka et al. |
| 6,770,087 B2 | 8/2004 | Layne et al. |
| 6,780,196 B2 | 8/2004 | Chin et al. |
| 6,786,920 B2 | 9/2004 | Shannon et al. |
| 6,790,225 B1 | 9/2004 | Shannon et al. |
| 6,802,851 B2 | 10/2004 | Jones et al. |
| 6,811,560 B2 | 11/2004 | Jones et al. |
| 6,855,153 B2 | 2/2005 | Saadat |
| 6,958,061 B2 | 10/2005 | Truckai et al. |
| 6,979,344 B2 | 12/2005 | Jones et al. |
| 7,029,487 B2 | 4/2006 | Greene, Jr. et al. |
| 7,052,513 B2 | 5/2006 | Thompson |
| 7,070,609 B2 | 7/2006 | West |
| 7,083,632 B2 | 8/2006 | Avellanet et al. |
| 7,083,643 B2 | 8/2006 | Whalen et al. |
| 7,153,323 B1 | 12/2006 | Teoh et al. |
| 7,156,871 B2 | 1/2007 | Jones et al. |
| 7,186,263 B2 | 3/2007 | Golds et al. |
| 7,201,762 B2 | 4/2007 | Greene, Jr. et al. |
| 7,211,109 B2 | 5/2007 | Thompson |
| 7,229,461 B2 | 6/2007 | Chin et al. |
| 7,232,461 B2 * | 6/2007 | Ramer .................. 623/1.28 |
| 7,306,622 B2 | 12/2007 | Jones et al. |
| 7,306,624 B2 | 12/2007 | Yodfat et al. |
| 7,314,484 B2 * | 1/2008 | Deem et al. ........... 623/1.36 |
| 7,491,214 B2 | 2/2009 | Greene, Jr. et al. |
| 7,530,988 B2 | 5/2009 | Evans et al. |
| 7,572,288 B2 | 8/2009 | Cox |
| 7,608,088 B2 | 10/2009 | Jones et al. |
| 7,611,530 B2 | 11/2009 | Pomeranz et al. |
| 7,621,928 B2 | 11/2009 | Thramann et al. |
| 7,637,942 B2 | 12/2009 | Mangiardi et al. |
| 7,666,220 B2 | 2/2010 | Evans et al. |
| 2001/0047202 A1 * | 11/2001 | Slaikeu et al. ............ 623/1.46 |
| 2002/0042628 A1 | 4/2002 | Chin et al. |
| 2002/0169473 A1 | 11/2002 | Sepetka et al. |
| 2003/0083676 A1 | 5/2003 | Wallace |
| 2003/0093097 A1 | 5/2003 | Avellanet et al. |
| 2003/0135264 A1 | 7/2003 | Whalen et al. |
| 2003/0181927 A1 | 9/2003 | Wallace |
| 2003/0187473 A1 | 10/2003 | Berenstein et al. |
| 2003/0195553 A1 | 10/2003 | Wallace et al. |
| 2004/0098027 A1 | 5/2004 | Teoh et al. |
| 2004/0098097 A1 | 5/2004 | Fogarty et al. |
| 2004/0158282 A1 | 8/2004 | Jones et al. |
| 2004/0181253 A1 | 9/2004 | Sepetka et al. |
| 2005/0021077 A1 | 1/2005 | Chin et al. |
| 2005/0033349 A1 | 2/2005 | Jones et al. |
| 2005/0267510 A1 | 12/2005 | Razack |
| 2006/0052816 A1 | 3/2006 | Bates et al. |
| 2006/0058834 A1 | 3/2006 | Do et al. |
| 2006/0079923 A1 | 4/2006 | Chhabra et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0155323 A1 | 7/2006 | Porter et al. |
| 2006/0200234 A1 * | 9/2006 | Hines ..................... 623/1.49 |
| 2006/0206139 A1 | 9/2006 | Tekulve |
| 2006/0206196 A1 | 9/2006 | Porter |
| 2006/0206199 A1 * | 9/2006 | Churchwell et al. ......... 623/1.25 |
| 2006/0235464 A1 | 10/2006 | Avellanet et al. |
| 2006/0276831 A1 | 12/2006 | Porter et al. |
| 2006/0292206 A1 | 12/2006 | Kim et al. |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0067015 A1 * | 3/2007 | Jones et al. ................. 623/1.15 |
| 2007/0088387 A1 | 4/2007 | Eskridge et al. |
| 2007/0106311 A1 | 5/2007 | Wallace et al. |
| 2007/0150041 A1 | 6/2007 | Evans et al. |
| 2007/0168011 A1 | 7/2007 | LaDuca et al. |
| 2007/0207186 A1 | 9/2007 | Scanlon et al. |
| 2007/0219610 A1 | 9/2007 | Israel |
| 2007/0219619 A1 | 9/2007 | Dieck et al. |
| 2007/0225794 A1 | 9/2007 | Thramann et al. |
| 2007/0239261 A1 | 10/2007 | Bose et al. |
| 2007/0276469 A1 | 11/2007 | Tenne |
| 2007/0276470 A1 | 11/2007 | Tenne |
| 2008/0004653 A1 | 1/2008 | Sherman et al. |
| 2008/0033341 A1 | 2/2008 | Grad |
| 2008/0033480 A1 | 2/2008 | Hardert |
| 2008/0039933 A1 | 2/2008 | Yodfat et al. |
| 2008/0147100 A1 | 6/2008 | Wallace |
| 2008/0161936 A1 | 7/2008 | Feller et al. |
| 2008/0195137 A1 | 8/2008 | Alleyne et al. |
| 2008/0275536 A1 * | 11/2008 | Zarins et al. ................. 623/1.11 |
| 2008/0319521 A1 | 12/2008 | Norris et al. |
| 2009/0287288 A1 * | 11/2009 | Berez et al. .................... 623/1.2 |
| 2009/0318949 A1 * | 12/2009 | Ganpath et al. ............... 606/192 |

\* cited by examiner

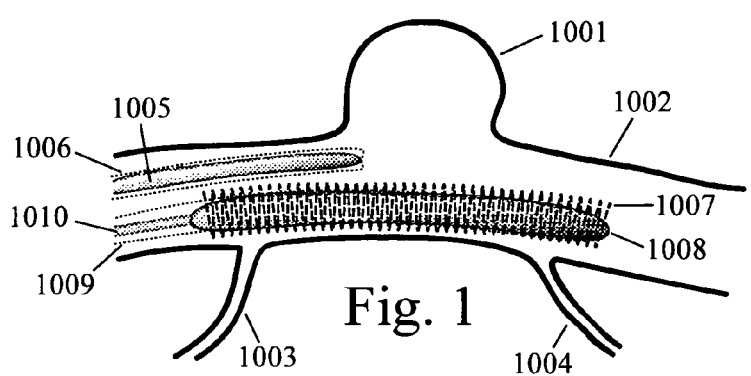
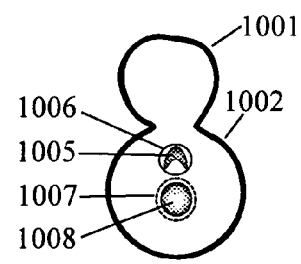
Fig. 1      Fig. 2
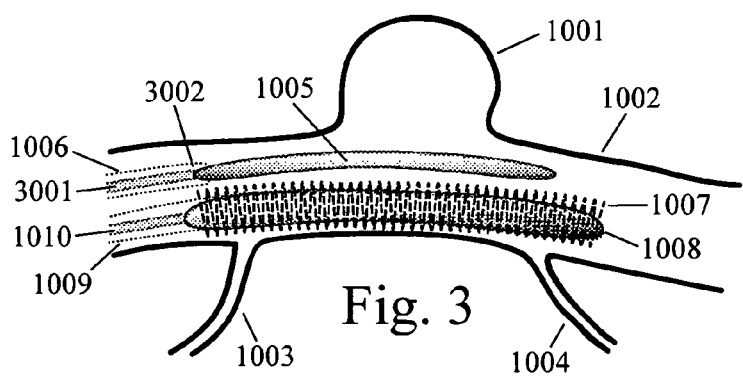
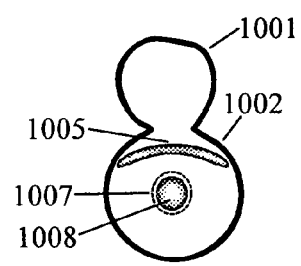
Fig. 3      Fig. 4
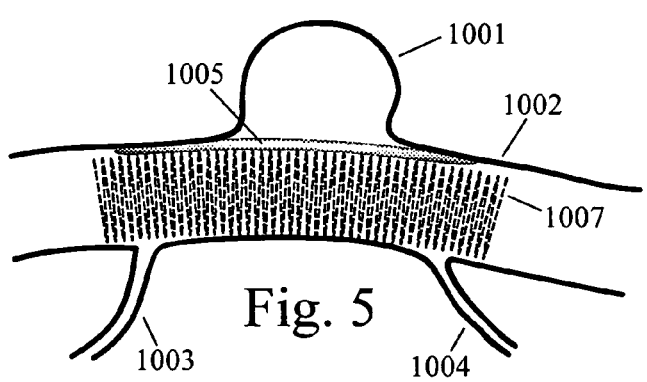
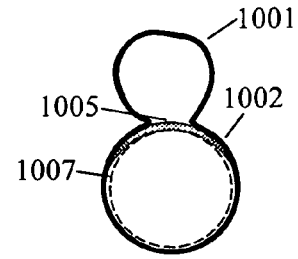
Fig. 5      Fig. 6

OCCLUDING MEMBER EXPANSION AND THEN STENT EXPANSION FOR ANEURYSM TREATMENT

CROSS-REFERENCE TO RELATED APPLICATIONS

This patent application claims the priority benefit of U.S. Provisional Patent Application No. 61/398,918 entitled "Occluding Member Expansion and then Stent Expansion for Aneurysm Treatment" filed on Jul. 1, 2010 by Robert A. Connor.

FEDERALLY SPONSORED RESEARCH

Not Applicable

SEQUENCE LISTING OR PROGRAM

Not Applicable

BACKGROUND

Field of Invention

This invention relates to treatment of aneurysms.

INTRODUCTION TO CEREBRAL ANEURYSMS

An aneurysm is an abnormal localized bulging or ballooning of all the layers of the wall of a blood vessel. This condition results in a blood-filled sac or bulge extending outwards from the parent blood vessel. "Saccular aneurysms" (also called "berry aneurysms") look like a sac protruding out from the parent vessel. Saccular aneurysms have a neck (which may be relatively narrow or wide) and are prone to growth and rupture. Larger aneurysms are more likely to rupture. Wide neck aneurysms are less likely to rupture, but are harder to treat. "Fusiform aneurysms" are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particular for saccular aneurysms, increases the risk of the aneurysm hemorrhaging blood into the surrounding tissue through a leak or a complete rupture, with serious and possibly fatal health outcomes.

Cerebral aneurysms, also called "brain aneurysms" or "intracranial aneurysms," are aneurysms that occur in the intercerebral arteries that supply blood to the brain. The vast majority of cerebral aneurysms form in the junction of arteries at the base of the brain that is known as the Circle of Willis where arteries come together and from which these arteries send branches to different areas of the brain. The fluid dynamics of blood flow through this junction put relatively-high pressure on certain places along the vessel walls. Weak spots form in the vessel walls where the arteries come together in this circle. Cerebral aneurysms are generally saccular aneurysms.

The subarachnoid space is between the arachnoid membrane and the pia mater surrounding the brain. When the rupture of a cerebral aneurysm releases blood into this space, this event is called a Subarachnoid Hemorrhage or "SAH". An SAH is a serious health hazard. The results of biodegrading blood products from the escaped blood can cause spasm and contraction of the smooth muscle cells in the walls of cerebral blood vessels (a condition called "cerebral vasospasm"). Contraction of these blood vessel walls can restrict blood flow to downstream tissue, depriving that tissue of oxygen (a condition called "Delayed Ischemic Neurological Deficit" or "DIND"), leading to brain tissue necrosis. Approximately one-third to one-half of people with an SAH die within one month and, of those who survive, approximately one-half suffer significant loss of brain function and are unable to function independently afterwards.

Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm will die within one month of the rupture. Sadly, even among those who survive, approximately one-half suffer significant and permanent deterioration of brain function.

Surgical clipping of aneurysms (insertion of a compressive clamp on the outside of aneurysm neck) was developed during the 1930's and is well-established. However, surgical clipping requires relatively invasive surgery with attendant risks and long recovery times. During the past three decades a variety of alternative methods for treating cerebral aneurysms have been developed. This development has been marked by two general trends. First, there has been a general trend away from surgical clipping toward less-invasive endovascular methods of treating aneurysms. Second, there has been an overall evolution in the less-invasive endovascular methods—evolving from permanent balloons implanted into the aneurysm, to permanent coils implanted into the aneurysm, to permanent stents or temporary balloons deployed in the parent vessel before insertion of coils into the aneurysm (sometimes called "stent-assisted coiling" or "jailing"), to specialized neurological stents that reconstruct the parent vessel to address the hemodynamic conditions that contributed to formation of the aneurysm in the first place.

Despite the variety of alternative methods that have been developed during the past three decades, there remains a significant clinical need for better devices and methods to treat cerebral aneurysms. There is still significant mortality and morbidity from cerebral aneurysms with current devices and methods. Also, there are still types of aneurysms (such as wide-neck saccular aneurysms and aneurysms located near branching vessels) that are difficult to treat with current devices and methods.

CATEGORIZATION AND REVIEW OF THE ART

We now review the prior art. To provide a conceptual framework for this review, we categorize devices and methods into ten general categories. We note the limitations of each category and afterwards discuss how this current invention can address these limitations. Before discussing these ten categories in detail, we first list all ten in order to provide the reader with a conceptual overview of the art in this field.

The ten categories of devices and methods are as follows: (1) surgical placement of a clip onto the aneurysm neck from outside the vessel; (2) endovascular implantation of a permanent balloon inside the aneurysm; (3) endovascular insertion of embolic coils into the aneurysm; (4) endovascular deployment of non-coil solid embolic members into the aneurysm; (5) injection of a liquid or gel that congeals within the aneurysm; (6) deployment of a stent in the parent vessel of the aneurysm wherein this stent has a single layer with a uniform wall porosity; (7) deployment of a permanent stent (or temporary balloon) in the parent vessel followed by insertion of embolic coils or other embolic members into the aneurysm; (8) deployment of a stent in the parent vessel wherein this stent has an impermeable inner layer, an outer layer that conforms to the wall of the vessel, and filling the gap between the inner and outer stent layers; (9) deployment of a stent in the parent vessel wherein this stent is pre-formed with areas of differing wall porosity and a less-porous area is positioned over the aneurysm neck; and (10) deployment of a stent in the parent vessel wherein areas of differing wall porosity are created by modification of the stent wall surface after stent deployment. The last four categories of these ten appear to be most relevant to this present invention, so we cover them in greater detail, including identification of examples of prior art within these categories.

1) Clip on the Aneurysm from Outside the Vessel ("Clipping")

This first category of devices and methods involves surgical placement of a clip onto the neck of an aneurysm from outside the blood vessel. The use of a clip to clamp the neck of an aneurysm is often referred to as "clipping" although the action is compressive, not cutting, in nature. Clipping generally involves invasive surgery including a craniotomy, which entails temporarily removing a section of the skull. There are many different types of aneurysm clips in the prior art. Aneurysm clips are generally metal. They often have a pair of clamping arms that are connected by a flexible, spring-action loop. These arms are often opened by compressing the loop. Once open, the arms are positioned on either side of the aneurysm neck and then closed around the neck when compression of the loop is released. Clipping was developed by Walter Dandy at the Johns Hopkins Hospital in the 1930's and is well-established as a method of treating cerebral aneurysms, particularly aneurysms that have ruptured and are bleeding. However, the use of clipping is decreasing overall, particularly in Europe, due to the development of less-invasive methods for treating aneurysms.

Potential limitations of surgical clipping include: health risks, such as infection and body stress, associated with major surgery; relatively long recovery periods; risk of injury to other brain structures during the operation; risk of pinching and (further) rupturing the aneurysm neck; difficulty accessing aneurysms in some portions of the brain, even after removal of a section of the skull; difficulty clipping fusiform aneurysms; and failure to address the hemodynamics of the parent vessel that contributed to the formation of the aneurysm in the first place.

2) Balloon Inside the Aneurysm

This second category of devices and methods involves the endovascular implantation of a permanent balloon inside the aneurysm sac. This approach was pursued approximately three decades ago, including implantation of latex balloons into aneurysms, but was then largely abandoned due to the risks. Potential limitations of implantation of a permanent balloon inside the aneurysm include: very high rates (over 30%) of procedural morbidity and mortality; risk of balloon deflation; risk of balloon prolapse into the parent vessel; difficulty keeping balloon (by itself) inside fusiform and wide-neck saccular aneurysms; (further) aneurysm rupture during balloon inflation; recanalization (reoccurrence of blood flow through channels in the aneurysm) around the smooth surface of the balloon; and failure to address the hemodynamics of the parent vessel that contributed to the formation of the aneurysm in the first place.

3) Coils Inside the Aneurysm ("Coiling")

The next category of devices and methods involves endovascular insertion of flexible, detachable embolic coils into the aneurysm. Coils do not completely fill the volume of the aneurysm. Coils are delivered to the aneurysm through a catheter and then released into the aneurysm in a series of basically-random loops. It is generally easier to deploy coils in a small-neck aneurysm than in a wide-neck or fusiform aneurysm. The goal of coiling is to fill a sufficient percentage of the volume of the aneurysm that the flow of blood is reduced, the interior matter of the aneurysm embolizes, and vessel wall cells grow over the aneurysm neck.

Endovascular aneurysm coiling was developed in the early 1990's by Guido Guglielmi at UCLA. Historically, most aneurysm coils have been metal, primarily platinum. However, coils can also be made from other materials such as polymers and hydrogels. Coiling is less invasive and associated with shorter recovery periods than clipping. The results of the ISAT study also provide evidence that coiling has lower mortality rates than clipping for patients whose aneurysms have ruptured. Coiling is more common in Europe than in the U.S. In addition to stand-alone use of coiling, coiling can also be done following deployment of a stent or balloon in the parent vessel. These combination methods are often called "stent-assisted" or "balloon-assisted" coiling. We have created a separate category for such combination methods and discuss them separately below.

Potential limitations of unassisted coiling include: coils only fill a limited percentage of the volume ("packing density") of the aneurysm (less than 50% achieve complete angiographic occlusion in follow-up evaluation) and low volume occlusion is associated with a higher risk of recanalization and rupture; coils can compact over time, leading to recanalization (with recanalization rates in the range of 30%-50%); gaps between coils in the region of the aneurysm neck can allow persistent inflow and continued aneurysm growth; it is difficult to treat wide-neck or fusiform aneurysm with coils alone; coils can prolapse through the aneurysm neck into the parent vessel during or after the procedure; it is difficult to clip aneurysms that have been filled with metal coils if needed later; the coils can put undesirable pressure on surrounding brain tissue; there is a risk of puncturing the aneurysm wall with a metal coil; platinum coils can be expensive; there can be injury to a blood vessel during navigation of the catheter; clots from the aneurysm can escape into the parent vessel and cause a downstream stroke; there is a higher rate of aneurysm recurrence (approximately one out of three) after coiling than after clipping; and coiling does not correct the hemodynamics of the parent vessel that contributed to the formation of the aneurysm in the first place.

4) Non-Coil Solid Members into the Aneurysm

The next category of devices and methods involves endovascular insertion of one or more solid members, other than coils, into the aneurysm to seal off the neck, occlude the aneurysm, and/or reduce blood flow to the aneurysm. For example, there are flexible metal meshes that collapse into "hour-glass" shapes which compress onto both sides of the aneurysm neck—sealing off the neck. There are also expanding occlusive devices that are inserted into, and expand within, the aneurysm. This expansion may be self-expansion upon release from the constraints of a catheter (such as a device made from shape-memory material). Alternatively, this expansion may occur upon interaction with blood (such as a hydrogel plug). As another alternative, this expansion may be mechanically activated by the device operator.

Potential limitations of using non-coil solid members to seal the aneurysm neck or occlude the aneurysm include:

difficulty engaging the necks of wide-neck saccular or fusiform aneurysms; difficulty filling irregularly-shaped aneurysms with standard-shaped mesh structures and possible recanalization; risk of rupture when pinching the aneurysm neck or pushing on the aneurysm walls; protrusion of the proximal portion of "hour-glass" designs into the parent vessel; difficulty clipping aneurysms later that have been occluded in this manner; and these methods do not correct the hemodynamics of the parent vessel that contributed to the formation of the aneurysm in the first place.

5) Congealing Liquid or Gel into the Aneurysm

This category of devices and methods involves endovascular injection of a liquid or gel that congeals within the aneurysm. If this can be accomplished without having any of the liquid or gel escape out of the aneurysm, then it has several potential advantages over prior methods, including achieving rapid occlusion of a large volume of the aneurysm. Potential limitations of injecting a congealing liquid or gel into the aneurysm include: risk of leakage of the congealing substance into the parent vessel and causing a stroke downstream; difficulty filling the entire aneurysm if the substance begins to congeal before the aneurysm is full; seepage of toxic substances into the blood stream; difficulty of future clipping if liquid or gel solidifies into a relatively hard mass; and failure to correct the hemodynamics of the parent vessel that contributed to the formation of the aneurysm in the first place.

6) Stent with a Single Layer and Uniform Porosity in Parent Vessel

This category of devices and methods involves endovascular deployment of a stent in the parent vessel of the aneurysm, wherein the stent has a single layer and uniform porosity across all of its walls. Standard stents are highly porous, but specialized variations may be impermeable to blood flow. Such stents can be particularly useful for fusiform aneurysms. A stent of this type may be used to reconstruct the parent vessel to occlude the aneurysm and change the hemodynamics of the parent vessel that contributed to the formation of the aneurysm. The portion of the stent covering the aneurysm neck may reduce the pulsing force of blood against the aneurysm wall and also serve as a scaffolding for growth of endothelial tissue across the neck.

Potential limitations of deploying a stent with a single layer and uniform porosity in the parent vessel include: a uniformly high-porosity stent may not adequately block blood flow into the aneurysm; a uniformly low-porosity stent may undesirably block blood flow to small branching vessels whose entrances from the parent vessel are covered by the stent; a uniformly low-porosity stent may not adequately frictionally engage the vessel wall; difficulty achieving a uniformly low-porosity stent with an expanding stent design.

7) Stent in Parent and then Embolic Members in Aneurysm ("Stent-Assisted Coiling")

This category of devices and methods involves first deploying a stent in the parent vessel of the aneurysm and then inserting embolic members, such as coils, into the aneurysm. This is called "stent-assisted coiling" or "jailing." The stent can stop the embolic members from prolapsing into the parent vessel. The stent can also help to correct the hemodynamics of the parent vessel that led to formation of the aneurysm in the first place. As a variation on this method, a balloon may be temporarily deployed in the parent vessel to help stop embolic members from prolapsing into the parent vessel, at least during insertion of the embolic members.

Potential limitations of first deploying a stent (or balloon) in the parent vessel and then inserting embolic members into the aneurysm include: difficulty injecting embolic members through the wall of the stent or between the expanded stent and the vessel wall; difficulty filling a high percentage of the aneurysm volume through the wall of the expanded stent; difficulty achieving a good seal around the neck of the aneurysm with a high-porosity stent; and difficulty inserting embolic members through the wall of a low-porosity stent.

Examples in the prior art that appear to fall into this category include: U.S. Pat. No. 6,096,034 (Kupiecki et al., 2000, "Aneurysm Closure Device Assembly"), U.S. Pat. No. 6,168,592 (Kupiecki et al., 2001, "Aneurysm Closure Device Assembly"), U.S. Pat. No. 6,344,041 (Kupiecki et al., 2002, "Aneurysm Closure Device Assembly"), U.S. Pat. No. 6,802,851 (Jones et al., 2004, "Stent Aneurysm Embolization Method using Collapsible Member and Embolic Coils"), U.S. Pat. No. 7,306,622 (Jones et al., 2007, "Stent Embolization Device"), U.S. Pat. No. 7,608,088 (Jones et al., 2009, "Stent Aneurysm Embolization Device"); and U.S. Patent Applications 20060206196 (Porter, 2006, "Device for Closure of a Vascular Defect and Method for Treating the Same), 20070150041 (Evans et al., 2007, "Methods and Systems for Aneurysm Treatment Using Filling Structures"), and 20080161936 (Feller et al., 2008, "Remodeling Device for Aneurysms").

8) Stent with Impermeable Inner Layer, Outer Layer Conforming to Vessel Wall, and Substance Filled Between Layers This category of devices and methods involves deployment of a stent in the parent vessel wherein this stent has an impermeable inner layer, this stent has an outer layer that conforms to the wall of the blood vessel, and the gap between the inner and outer layers is filled (generally with a congealing liquid or gel). Devices and methods in this category are generally shown in the prior art as being deployed within fusiform aortic aneurysms. Potential limitations of a stent with an inner impermeable layer, outer layer conforming to the vessel wall, and congealing filler in between these layers include: difficulty injecting congealing filler into the gap between the layers; risk that an embolizing liquid or gel will leak out and cause a stroke downstream; challenges containing the embolic material within curving vessels; and seepage of toxic substances into the blood stream.

Examples in the prior art that appear to fall into this category include: U.S. Pat. No. 5,769,882 (Fogarty et al. 1998 "Methods and Apparatus for Conformably Sealing Prostheses within Body Lumens"), U.S. Pat. No. 6,656,214 (Fogarty et al., 2003, "Methods and Apparatus for Conformably Sealing Prostheses within Body Lumens"), U.S. Pat. No. 7,530,988 (Evans et al., 2009, "Methods and Systems for Endovascular Aneurysm Treatment"), U.S. Pat. No. 7,666,220 (Evans et al., 2010, "System and Methods for Endovascular Aneurysm Treatment"); and U.S. Patent Applications 20040098097 (Fogarty et al., 2004, "Methods and Apparatus for Conformably Sealing Prostheses Within Body Lumens"), 20070061005 (Kim et al., 2007, "Devices and Methods for Treatment of Vascular Aneurysms"), and 20080195137 (Alleyne et al., 2008, "Devices and Methods for Aneurysm Treatment").

9) Stent with Pre-Formed Areas of Differing Porosity

This category of devices and methods involves deployment of a stent in the parent vessel wherein this stent is pre-formed with one or more areas of lower wall porosity and higher wall porosity. An area of lower wall porosity is positioned over the aneurysm neck to reduce blood flow to the aneurysm while areas of higher wall porosity are positioned over smaller vessels branching off from the parent vessel. Potential limitations of such stents with pre-formed areas of differing wall porosity include: difficulty matching a specific anatomic configuration (curvature, branching, neck size, etc) with a preformed stent; difficulty of precise placement of the stent to properly align the porous and non-porous areas with branching vessels and the aneurysm neck; and difficulty creating low porosity areas in a compressed state that maintain this low porosity in an expanded state.

Examples in the prior art that appear to fall into this category include: U.S. Pat. No. 5,723,004 (Dereume et al., 1998, "Expandable Supportive Endoluminal Grafts"), U.S. Pat. No. 5,769,884 (Solovay, 1998, "Controlled Porosity Endovascular Implant"), U.S. Pat. No. 5,948,018 (Dereume et al., 1999, "Expandable Supportive Endoluminal Grafts"), U.S. Pat. No. 6,165,212 (Dereume et al., 2000, "Expandable Supportive Endoluminal Grafts"), U.S. Pat. No. 6,309,367 (Boock, 2001, "Aneurysm Shield"), U.S. Pat. No. 6,309,413 (Dereume et al., 2001, "Expandable Supportive Endoluminal Grafts"), U.S. Pat. No. 7,232,461 (Ramer, 2007, "Neck Covering Device for an Aneurysm"), U.S. Pat. No. 7,621,928 (Thramann et al., 2009, Aneurysm Stent"), and U.S. Pat. No. 7,637,942 (Mangiardi et al., 2009, "Coated Stent with Geometry Determinated Functionality and Method of Making the Same"); and U.S. Patent Applications 20070219610 (Israel, 2007, "Stent with Flap"), 20070225794 (Thramann et al., 2007, "Aneurysm Stent"), and 20080004653 (Sherman et al., 2008, "Thin Film Devices for Occlusion of a Vessel").

10) Stent with Areas of Differing Porosity from Post-Expansion Surface Modification This category of devices and methods involves deployment of a stent in the parent vessel wherein areas of differing wall porosity are created by modification of the stent wall surface after stent expansion. For example, the portion of the stent wall covering the neck of an aneurysm may be made less porous. For example, a portion of the stent wall may be coated with a substance after deployment to make that portion less porous. As another example, a portion of the stent wall may be exposed to targeted energy emissions to make that portion less porous. As another example, slats or fibers may be added or removed from certain areas of the stent wall after deployment to make those areas less or more porous, respectively.

Potential limitations of such stents with areas of differing porosity from post-expansion surface modification include: negative effects of surface-modifying chemicals seeping into the blood stream; negative effects of energy emissions on surrounding vessels or brain tissue; and difficulty adding enough matter to the stent wall covering the aneurysm neck by chemical or energy modification means, after stent implantation, to adequately reduce blood flow through the aneurysm neck.

Examples in the prior art that appear to fall into this category include: U.S. Pat. No. 5,951,599 (McCrory, 1999, "Occlusion System for Endovascular Treatment of an Aneurysm"), U.S. Pat. No. 7,156,871 (Jones et al., 2007, "Expandable Stent Having a Stabilized Portion"), U.S. Pat. No. 7,572,288 (Cox, 2009, "Aneurysm Treatment Device and Method of Use"), and U.S. Pat. No. 7,611,530 (Pomeranz et al., 2009, "Expandable Stent Having Removable Slat Members"); and U.S. Patent Application 20070067015 (Jones et al., 2007, "Expandable Stent Having a Stabilized Portion").

SUMMARY AND ADVANTAGES OF THIS INVENTION

This invention is a device and method to occlude an aneurysm comprising: a laterally-expanding occluding member (such as a relatively flat balloon, mesh, net, or patch) that is positioned within the parent vessel of the aneurysm and then expanded laterally; and a radially-expanding structural member (such as a stent) that is positioned within the parent vessel of the aneurysm and then expanded radially after, or concurrently with, expansion of the laterally-expanding occluding member. Lateral expansion is primarily in directions that are parallel to the plane defined by the circumference of the aneurysm neck. The laterally-expanding member is expanded from a first configuration with a width that is less than the width of the aneurysm neck to a second configuration with a width that equals or exceeds the width of the aneurysm neck. Expansion of the radially-expanding member presses and holds the laterally-expanding occluding member into contact with the aneurysm neck, so that the laterally-expanding occlusive member at least partially covers the aneurysm neck and reduces blood flow to the aneurysm. The laterally-expanding occlusive member is substantially flat after expansion of the radially-expanding structural member. This invention has several potential advantages over devices and methods in the prior art, especially for treatment of wide-neck and fusiform aneurysms.

Potential advantages of this invention compared to clipping include: less invasive procedure; reduced health risks and shorter recovery periods; can be used for wide-neck and fusiform aneurysms; and helps to correct hemodynamics of the parent vessel that contributed to the formation of the aneurysm.

Potential advantages of this invention compared to a balloon include the aneurysm include: lower risk of post-procedural balloon deflation; lower risk of prolapse of embolic member into parent vessel; low risk of (further) aneurysm rupture during procedure; lower risk of recanalization; and helps to correct hemodynamics of the parent vessel that contributed to the formation of the aneurysm.

Potential advantages of this invention compared to stand-alone coiling include: much more complete sealing of aneurysm neck, especially reduced gaps around the circumference of the neck; more useful for wide-neck and fusiform aneurysms; no risk of prolapse of coils into parent vessel; easier to clip aneurysm neck afterwards, if necessary; low risk of puncturing aneurysm walls during deployment; avoid expense of platinum coils; and helps to correct hemodynamics of the parent vessel that contributed to the formation of the aneurysm.

Potential advantages of this invention compared to non-coil solid members deployed in the aneurysm include: easier to treat wide-neck saccular or fusiform aneurysms; aneurysm shape is not a limitation; no "pinching" the aneurysm neck during deployment and lower associated risk of (further) aneurysm rupture; easier clipping later, if necessary; and helps to correct hemodynamics of the parent vessel that contributed to the formation of the aneurysm.

Potential advantages of this invention compared to injection of a congealing liquid or gel into the aneurysm include: no risk of leaking congealing substance into the parent vessel and causing a stroke downstream; occlusion of full aneurysm volume is not necessary because neck is sealed off; no seepage of toxic substances into the blood stream; easier clipping later, if necessary; and helps to correct hemodynamics of the parent vessel that contributed to the formation of the aneurysm.

Potential advantages of this invention compared to a single-layer stent with uniform porosity in the parent vessel include: creates a low-porosity seal for the aneurysm neck, but still allows good blood flow to any nearby branching vessels that may be covered by the stent; achieving of low-porosity neck occlusion despite use of an expanding stent; and good engagement of the vessel wall by the stent.

Potential advantages of this invention compared to deploying a stent (or temporary balloon) in the parent vessel and then inserting embolic members into the aneurysm include: better seal around the neck of the aneurysm for reduced risk of recanalization and continued aneurysm growth; do not have to insert embolic members through the wall of the stent or between the expanded stent and the vessel wall; and easier to achieve low-porosity surface over the aneurysm neck.

Potential advantages of this invention compared to a stent in the parent vessel (wherein this stent has an impermeable inner layer, this stent has an outer layer that conforms to the wall of the blood vessel, and the gap between the inner and outer layers is filled with a congealing liquid or gel) include: no need to inject filler substance between stent layers; no risk of leakage of an embolizing liquid or gel that may cause a stroke downstream; and no risk of toxic substances seeping into the blood stream.

Potential advantages of this invention compared to a stent in the parent vessel with pre-formed areas of differing porosity include: avoid need to precisely position a stent in the parent vessel so that its low-porosity area covers the aneurysm neck; and easier to create a low-porosity structure to provide a good seal for the aneurysm neck than with an expandable stent alone.

Potential advantages of this invention compared to a stent in the parent vessel with areas of differing porosity that are created from modification of the stent surface after their expansion include: no negative effects of surface-modifying chemicals seeping into the blood stream; no negative effects of energy emissions on surrounding vessels or brain tissue; and no difficulty adding enough matter to the stent wall covering the aneurysm neck by chemical or energy modification means, after stent implantation, to adequately reduce blood flow through the aneurysm neck.

INTRODUCTION TO THE FIGURES

FIGS. 1 through 12 provide two different cross-sectional perspectives of a three-sequence series that shows how two embodiments of this invention can be deployed. These are only two of the possible embodiments and these figures do not limit the full generalizability of the claims.

FIGS. 1 through 6 show three stages of deployment of the first embodiment that employs a relatively-flat balloon as a laterally-expanding occluding member and a stent as a radially-expanding structural member.

DETAILED DESCRIPTION OF THE FIGURES

Figure 7:
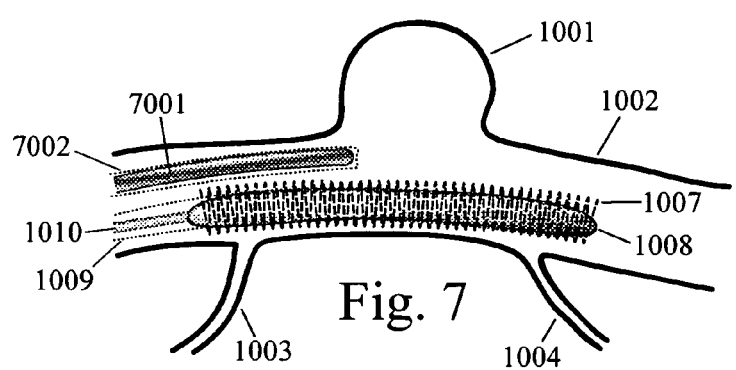
FIGS. 7 through 12 show three stages of deployment of the second embodiment that employs a self-expanding foam patch as a laterally-expanding occluding member and again uses a stent as a radially-expanding structural member.

FIGS. 1 through 12 provide two different cross-sectional perspectives of a three-sequence series that shows how two embodiments of this invention can be deployed. These are only two of the possible embodiments and these figures do not limit the full generalizability of the claims. FIGS. 1 through 6 provide two different cross-sectional perspectives of a three-sequence series for a first embodiment of this invention to occlude an aneurysm. This first embodiment employs a relatively-flat balloon as a laterally-expanding occluding member and a stent as a radially-expanding structural member. FIGS. 7 through 12 provide two different cross-sectional perspectives of a three-sequence series for a second embodiment of this invention. This second embodiment employs a self-expanding foam patch as a laterally-expanding occluding member and again uses a stent as a radially-expanding structural member. We now discuss FIGS. 1 through 12 in detail.

FIG. 1 shows a longitudinal cross-sectional perspective of the first stage of deployment of this first embodiment in the parent blood vessel of an aneurysm. This first embodiment employs a relatively-flat balloon as a laterally-expanding occluding member and a stent as a radially-expanding structural member. In FIG. 1, aneurysm 1001, with a relatively wide neck, is shown bulging from the top of parent blood vessel 1002. Smaller blood vessels, 1003 and 1004, are shown branching off from the bottom of parent vessel 1002.

In FIG. 1, catheter 1006, containing laterally-expanding occluding member 1005, has been inserted into parent vessel 1002. In this example, laterally-expanding occluding member 1005 is a relatively-flat balloon that has been temporarily cross-sectionally inwardly-curved to fit within the diameter of catheter 1006 for navigation through the patient's vasculature and for insertion into the parent blood vessel of the aneurysm. Radially-expanding structural member 1007, with balloon 1008 in its core to power its expansion, has also been inserted into parent blood vessel 1002. In this example, the radially-expanding structural member 1007 is a stent. Many different types of radially-expanding stents, and balloons to power their expansion, are known in the prior art and the specifics of this stent and balloon are not central features of this invention.

Radially-expanding structural member 1007 spans the section of parent vessel 1002 that includes the neck of aneurysm 1001. Further, radially-expanding structural member 1007 is positioned on the side of laterally-expanding occluding member 1005 that faces away from the neck of aneurysm 1001. In this manner, laterally-expanding occluding member 1005 is located between radially-expanding structural member 1007 and the neck of aneurysm 1001. Catheter 1009 is used to insert radially-expanding structural member 1007 into the parent vessel and to enclose lumen 1010 which is used to inflate balloon 1008.

In this example, laterally-expanding occlusive member 1005 and radially-expanding structural member 1007 are inserted separately into the parent vessel. In another example, laterally-expanding occlusive member 1005 and radially-expanding structural member 1007 may be connected as an integrated device and inserted together into the parent vessel. In this example, laterally-expanding occlusive member 1005 is a relatively-flat balloon. In other examples, the laterally-expanding occlusive member may be selected from the group consisting of: a mesh; a net; a lattice; a membrane; a layer of fabric; a layer of shape memory material; and a substantially flat patch of compressible material.

Laterally-expanding occlusive member 1005 and radially-expanding structural member 1007 may be made of radio-opaque materials or other materials that appear different than surrounding tissue in medical imaging. This can help an operator to navigate them through the patient's vasculature, to position them in proximity to the aneurysm neck, and to coordinate their expansions. In various examples, the laterally-expanding occlusive member may be made from one or more of the following materials: ethylene propylene diene monomer (EPDM), latex, silicone, polytetrafluoroethylene (PFTE), polyvinyl chloride, and polyurethane. In various examples, the radially-expanding structural member may be made from one or more of the following materials: stainless steel, a nickel-titanium alloy, cobalt chromium or a cobalt-chromium alloy, titanium or a titanium alloy, tantalum or a tantalum allow, or polymeric-based resin or another polymer.

FIG. 2 shows an alternative perspective of the same first stage of implementation for the first embodiment that was introduced in FIG. 1. In particular, FIG. 2 shows a lateral cross-sectional perspective of the parent blood vessel 1002 and the aneurysm 1001. In FIG. 2, aneurysm 1001 is again shown bulging from the top of parent vessel 1002. The cross-sectional view of catheter 1006 in FIG. 2 more clearly shows how laterally-expanding occluding member 1005 (a relatively flat balloon in this example) has been inwardly-curved and constrained to fit into catheter 1006, before its release and lateral expansion. FIG. 2 also shows a cross-section of radially-expanding structural member 1007 (a stent in this example) with expansion-powering balloon 1008 in its core.

FIG. 3 shows a longitudinal cross-sectional perspective of the second stage of implementation of this first embodiment. In FIG. 3, laterally-expandable occlusive member 1005 has been pushed forward out of catheter 1006 so that it underlies the neck of aneurysm 1001. The same result may be achieved by retracting catheter 1006 backwards to expose laterally-expandable occlusive member 1005. Further, in FIG. 3, laterally-expandable occlusive member 1005 has been expanded laterally so that it more than spans the neck of aneurysm 1001. This lateral expansion is more clearly seen in the lateral cross-sectional perspective provided by FIG. 4 than the longitudinal cross-sectional perspective provided by FIG. 3. Lateral expansion is primarily in directions that are parallel to the plane defined by the circumference of the aneurysm neck. The laterally-expanding member is expanded from a first configuration with a width that is less than the width of the aneurysm neck to a second configuration with a width that equals or exceeds the width of the aneurysm neck. The laterally-expanding occlusive member is substantially flat after expansion of the radially-expanding structural member.

In this example, laterally-expanding occlusive member 1005 is a relatively-flat balloon that is expanded by filling it with a sterile saline solution that is delivered through lumen 3001. In other examples, a laterally-expanding occlusive member may be expanded by a means selected from the group consisting of: filling it with a gas; filling it with a liquid; filling it with a gel; and filling it with a plurality of solid or semi-solid members, which may be delivered in a flow of sterile saline solution. In another example, the laterally-expanding occlusive member may be expanded by chemical interaction between the material of the occlusive member and blood (or other matter in the parent vessel). For example, laterally-occlusive occluding member may be a hydrogel. In another example, the laterally-expanding occlusive member may be expanded by energy interaction between the material of the occlusive member and temperature in the parent vessel or directed energy from an artificial energy source. In another example, laterally-expanding occlusive member may be expanded by operation of Micro-Electro-Mechanical Systems (MEMS). In another example, the laterally-expanding occlusive member may self-expand when released from the constraints of a structure, such as a catheter, that is used to navigate it through the patient's vasculature and to position it within the parent blood vessel. As an example of the latter, the laterally-expanding occlusive member may be coiled, folded, or otherwise radially compressed to fit it into a catheter and it may expand out laterally into a relatively flat patch when it is released from the constraints of that catheter.

FIG. 5 shows a longitudinal cross-sectional perspective of the third stage of implementation of this first embodiment. FIG. 6 shows the corresponding lateral cross-sectional perspective of this third stage of implementation. In FIG. 5, catheter 1006 and lumen 3001 have been detached from laterally-expandable occlusive member 1005 and have been withdrawn from the parent vessel and the patient's body. In this example, this detachment is done by application of a modest electric pulse to meltable link 3002. Further, in FIG. 5, radially-expandable structural member 1007 has been expanded by inflation of balloon 1008. Balloon 1008, catheter 1009, and lumen 1010 were then withdrawn from the core of the stent, from the parent vessel, and from the patient's body entirely. Radially-expanding structural member 1007 has been expanded from a first configuration with a first diameter to a second configuration with a second diameter, wherein the second diameter is larger than the first diameter. Radially-expanding structural member 1007 is sufficiently structurally resilient to maintain the second configuration after its expansion within the parent vessel and the withdrawal of the balloon from its core.

As shown in FIGS. 5 and 6, expansion of radially-expanding structural member 1007 presses and holds laterally-expanding occluding member 1005 into contact with the neck of aneurysm 1001 so that laterally-expanding occlusive member 1001 covers the aneurysm neck and reduces blood flow into aneurysm 1001. Radially-expanding structural member 1007 has sufficient structural strength to hold laterally-expanding occlusive member 1005 against the neck of aneurysm 1001 so as to occlude the aneurysm neck. However, radially-expanding structural member 1007 is also sufficiently porous to allow blood flow to vessels 1003 and 1004 that branch from the parent vessel, wherein the entrances to vessels 1003 and 1004 are covered by the radially-expanding structural member 1007. The ability to selectively block blood flow to the aneurysm but not block blood flow to nearby branching vessels is an advantage of this invention over prior art involving stents with uniform porosity, whether that uniform porosity be low, mid-range, or high.

In an example, laterally-expanding occlusive member 1005 may have a porosity that is sufficiently high to allow blood to escape from aneurysm 1001 while occlusive member 1005 is being pressed against the neck of aneurysm 1001 by expansion of radially-expanding structural member 1007, but is sufficiently low to reduce blood flow to aneurysm 1001 after deployment. In an example, laterally-expanding occlusive member 1005 may be expanded by filling with a gas, liquid, or gel and some portion of the gas, liquid, or gel that filled this member may be allowed to escape from this member during expansion of the radially-expanding structural member. This allows the laterally-expanding occluding member to form a good seal against the aneurysm without impeding circular remodeling of the parent vessel by full radial expansion of the radially-expanding structural member. It can also help to avoid excessive pressure on the aneurysm neck as the radially-expanding structural member is being expanded.

In this invention, expansion of radially-expanding structural member 1007 occurs after, or concurrently with, expansion of the laterally-expanding occluding member 1005. This provides more thorough coverage and sealing of the aneurysm neck than is possible with devices and methods in the prior art wherein a stent is expanded first and then embolic members are inserted through the wall of the stent into the aneurysm. In such devices and methods in the prior art, embolic members may be "jailed" in the aneurysm, which is good for avoiding their prolapse into the parent vessel, but there can be gaps between the inserted embolic members and the perimeter of the aneurysm neck which can lead to recanalization. These gaps and this recanalization can be greatly reduced, or even avoided entirely, by the device and method disclosed herein. In this example, radially-expanding structural member 1007 is expanded after the expansion of laterally-expanding occlusive member 1005. In another example, radially-expanding structural member may be expanded concurrently with the expansion of laterally-expanding occlusive member 1005.

FIGS. 7 through 12 provide two different cross-sectional perspectives of a three-sequence series for a second embodiment of this invention to occlude an aneurysm. Like the first embodiment that was shown in FIGS. 1 through 6, this second embodiment uses a stent as a radially-expanding structural member. However, unlike the first embodiment, this second embodiment shown in FIGS. 7 through 12 employs a self-expanding foam patch as a laterally-expanding occluding member. FIG. 7 shows a longitudinal cross-sectional perspective of the first stage of implementation of this second embodiment. In FIG. 7, aneurysm 1001, with a relatively wide neck, is shown bulging from the top of parent blood vessel 1002. Smaller blood vessels, 1003 and 1004, are shown branching off from the bottom of parent vessel 1002.

In FIG. 7, catheter 7002, containing laterally-expanding occluding member 7001, has been inserted into parent vessel 1002. In this example, laterally-expanding occluding member 7001 is a self-expanding foam patch that has been temporarily cross-sectionally coiled to fit within the diameter of catheter 7002 for navigation through the patient's circulatory system and insertion into the parent vessel. Radially-expanding structural member 1007, with balloon 1008 within its core to power its expansion, has also been inserted in parent blood vessel 1002. In this example, radially-expanding structural member 1007 is once again a stent.

Radially-expanding structural member 1007 spans the section of parent vessel 1002 that includes the neck of aneurysm 1001. Further, radially-expanding structural member 1007 is positioned on the side of laterally-expanding occluding member 7001 that faces away from the neck of aneurysm 1001. In this manner, laterally-expanding occluding member 7001 is located between radially-expanding structural member 1007 and the neck of aneurysm 1001. Catheter 1009 is used to insert radially-expanding structural member 1007 into the parent vessel and to enclose lumen 1010 which is used to inflate balloon 1008.

In this example, laterally-expanding occlusive member 7001 and radially-expanding structural member 1007 are inserted separately into the parent vessel. In another example, laterally-expanding occlusive member 7001 and radially-expanding structural member 1007 may be connected as an integrated device and inserted together into the parent vessel. In this example, laterally-expanding occlusive member 7001 is a self-expanding foam patch. In other examples, the laterally-expanding occlusive member may be selected from the group consisting of: a mesh; a net; a lattice; a membrane; a layer of fabric; and a layer of shape-memory material.

Laterally-expanding occlusive member 7001 and radially-expanding structural member 1007 may be made of radio-opaque materials or other materials that are different in appearance from surrounding tissue in medical imaging. This can help an operator navigate them through the patient's vasculature, position them in proximity to the aneurysm neck, and coordinate their expansions. In various examples, the laterally-expanding occlusive member may be made from one or more of the following materials: Cross-Linked Polyethylene, Ethafoam polyethylene, Ether-Like-Ester (ELE), Latex, Polyester Polyurethane, Polytetrafluoroethylene (PFTE), Polyurethane, Silicone, and Zotefoam Polyethylene. In various examples, the radially-expanding structural member may be made from one or more of the following materials: stainless steel, a nickel-titanium alloy, cobalt chromium or a cobalt-chromium alloy, titanium or a titanium alloy, tantalum or a tantalum allow, or polymeric-based resin or another polymer.

Figure 8:
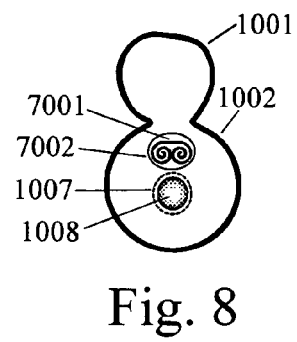

FIG. 8 shows an alternative perspective of the same first stage of implementation for this second embodiment that is shown in FIG. 7. The cross-sectional view of catheter 7002 in FIG. 8 more clearly shows how laterally-expanding occluding member 7001 (a self-expanding foam patch in this example) has been inwardly-coiled and constrained to fit into catheter 7002, before its release and lateral expansion. FIG. 8 also shows a cross-section of radially-expanding structural member 1007 (a stent in this example) with expansion-powering balloon 1008 inside its core.

Figure 9:
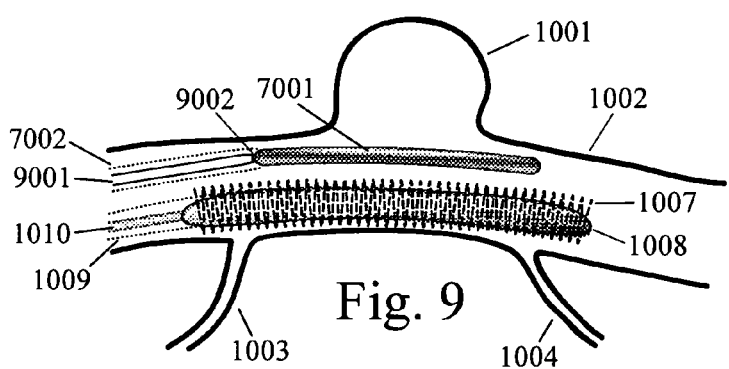
Figure 10:
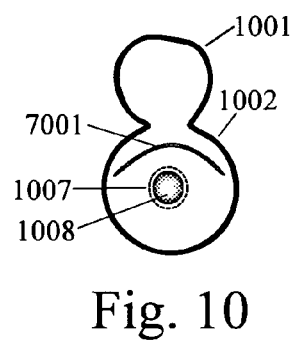

FIG. 9 shows a longitudinal cross-sectional perspective of the second stage of implementation of this second embodiment. In FIG. 9, laterally-expandable occlusive member 7001 has been pushed forward out of catheter 7002 by cable member 9001. The same result may be achieved by retracting catheter 7002 backwards to expose laterally-expandable occlusive member 7001. Further, in FIG. 9, laterally-expandable occlusive member 7001 has been expanded laterally so that it more than spans the neck of aneurysm 1001. In this example, laterally-expanding occlusive member 7001 is a self-expanding foam patch that self-expands when released from catheter 7002. This lateral expansion is more clearly seen in the lateral cross-sectional perspective provided by FIG. 10 than in the longitudinal cross-sectional perspective provided by FIG. 9. Lateral expansion is primarily in directions that are parallel to the plane defined by the circumference of the aneurysm neck. The laterally-expanding member is expanded from a first configuration with a width that is less than the width of the aneurysm neck to a second configuration with a width that equals or exceeds the width of the aneurysm neck. The laterally-expanding occlusive member is substantially flat after expansion of the radially-expanding structural member.

Figure 11:
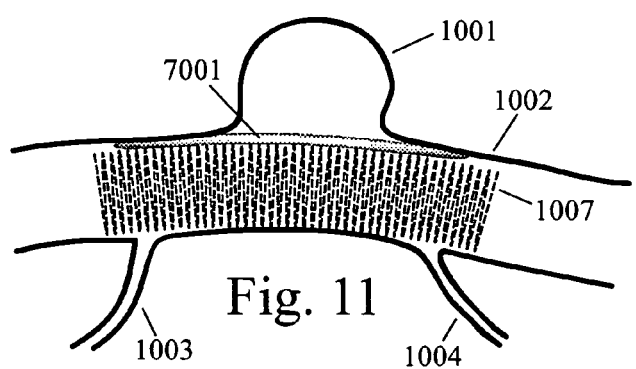
Figure 12:
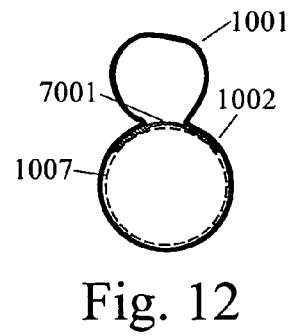

FIG. 11 shows a longitudinal cross-sectional perspective of the third stage of implementation of this second embodiment. FIG. 12 shows the corresponding lateral cross-sectional perspective of this third stage. In FIG. 11, catheter 7002 and cable member 9001 have been detached from laterally-expandable occlusive member 7001 and have been withdrawn from the parent vessel and the patient's body. In this example, this detachment is done by application of a modest electric pulse to meltable link 9002. Further, in FIG. 11, radially-expandable structural member 1007 has been expanded by inflation of balloon 1008. Balloon 1008, catheter 1009, and lumen 1010 were then withdrawn from the core of the stent, from the parent vessel, and from the patient's body entirely. Radially-expanding structural member 1007 is sufficiently structurally resilient to maintain the second configuration after its expansion within the parent vessel and the withdrawal of the balloon from its core.

As shown in FIGS. 11 and 12, expansion of radially-expanding structural member 1007 presses and holds laterally-expanding occluding member 7001 into contact with the neck of aneurysm 1001 so that laterally-expanding occlusive member 1001 covers the aneurysm neck and reduces blood flow into aneurysm 1001. Radially-expanding structural member 1007 has sufficient structural strength to hold laterally-expanding occlusive member 7001 against the neck of aneurysm 1001 so as to occlude the aneurysm neck. However, radially-expanding structural member 1007 is also sufficiently porous to allow blood flow to vessels 1003 and 1004 that branch from the parent vessel, wherein the entrances to vessels 1003 and 1004 are covered by the radially-expanding structural member 1007. The ability to block blood flow to the aneurysm but not block blood flow to nearby branching vessels is an advantage of this invention over prior art involving stents with uniform porosity, whether that uniform porosity be low, mid-range, or high.

In an example, laterally-expanding occlusive member 7001 may have a porosity that is sufficiently high to allow blood to escape from aneurysm 1001 while occlusive member 7001 is being pressed against the neck of aneurysm 1001 by expansion of radially-expanding structural member 1007, but is sufficiently low to reduce blood flow to aneurysm 1001 after deployment.

In this invention, expansion of radially-expanding structural member 1007 occurs after, or concurrently with, expansion of the laterally-expanding occluding member 7001. This provides more thorough coverage and sealing of the aneurysm neck than is possible with devices and methods in the prior art wherein a stent is expanded first and then embolic members are inserted through the wall of the stent into the aneurysm. In such devices and methods in the prior art, embolic members may be "jailed" in the aneurysm, which is good for avoiding their prolapse into the parent vessel, but there can be gaps between the inserted embolic members and the perimeter of the aneurysm neck which can lead to recanalization. These gaps and this recanalization can be greatly reduced, or even avoided entirely, by the device and method disclosed herein. In this example, radially-expanding structural member 1007 is expanded after the expansion of the laterally-expanding occlusive member 7001. In another example, radially-expanding structural member may be expanded concurrently with the expansion of the laterally-expanding occlusive member 7001.

I claim:

1. A device to occlude an aneurysm comprising:
 a laterally-expanding occluding member that is configured to be positioned within a parent vessel of the aneurysm and then expanded laterally;
 wherein the lateral expansion is primarily in directions that are configured to be parallel to a plane defined by a circumference of an aneurysm neck; and
 wherein the laterally expanding occluding member is expanded from a first configuration with a first width to a second configuration with a second width, wherein the second width is wider than the first width; and
 a radially-expanding structural member that is configured to be positioned within the parent vessel of the aneurysm and then expanded radially;
 wherein the radially-expanding structural member is configured to span a section of the parent vessel that includes the aneurysm neck;
 wherein the radially-expanding structural member is expanded from a first configuration with a first diameter to a second configuration with a second diameter, wherein the second diameter is larger than the first diameter;
 wherein the radially-expanding structural member is structurally resilient to maintain the second configuration after expansion while the radially-expanding structural member is configured to be within the parent vessel;
 wherein the radially-expanding structural member is positioned on a side of the laterally-expanding occluding member that is configured to face away from the aneurysm neck, such that the laterally-expanding occluding member is configured to be between the radially-expanding structural member and the aneurysm neck; and
 wherein expansion of the radially-expanding structural member presses and holds the laterally-expanding occluding member such that the laterally-expanding occluding member is configured to be in direct contact with the aneurysm neck, so that the laterally-expanding occluding member is configured to be at least partially covering the aneurysm neck and reduces blood flow to the aneurysm.

2. The device to occlude the aneurysm of claim 1, wherein the radially-expanding structural member is expanded after expansion of the laterally-expanding occlusive member.

3. The device to occlude the aneurysm of claim 1, wherein the radially-expanding structural member is expanded concurrently with expansion of the laterally-expanding occlusive member.

4. The device to occlude the aneurysm of claim 1, wherein the laterally-expanding occluding member is substantially flat after expansion of the radially-expanding structural member.

5. The device to occlude the aneurysm of claim 1, wherein the laterally-expanding occluding member is expanded by a means selected from the group consisting of: filling it with a gas; filling it with a liquid or gel; and filling it with a plurality of solid or semi-solid members.

6. The device to occlude the aneurysm of claim 1, wherein the laterally-expanding occluding member is expanded by chemical interaction configured to be between a material of the laterally-expanding occluding member and blood or other matter in the parent vessel.

7. The device to occlude the aneurysm of claim 1, wherein the laterally-expanding occluding member is expanded by energy interaction configured to be between a material of the laterally-expanding occluding member and temperature in the parent vessel or directed energy from an artificial energy source.

8. The device to occlude the aneurysm of claim 1, wherein the laterally-expanding occluding member is expanded by Micro-Electro-Mechanical Systems (MEMS).

9. The device to occlude the aneurysm of claim 1, wherein the laterally-expanding occluding member self-expands when released from the constraints of a catheter that is configured to insert the laterally-expanding occluding member into the parent vessel.

10. The device to occlude the aneurysm of claim 1, wherein the laterally-expanding occluding member is selected from the group consisting of: a balloon; a mesh; a net; a lattice; a membrane; a layer of fabric; a layer of shape memory material; and a substantially flat patch.

11. The device to occlude the aneurysm of claim 1, wherein the laterally-expanding occluding member has a porosity that is sufficiently high to allow blood to escape from the aneurysm while the laterally-expanding occluding member is configured to be pressed against the aneurysm neck by expansion of the radially-expanding structural member, but is sufficiently low to reduce blood flow to the aneurysm after deployment.

12. The device to occlude the aneurysm of claim 1, wherein the laterally-expanding occluding member is expanded by filling with a gas, liquid, or a gel and wherein some portion of the gas, liquid, or gel that filled the laterally-expanding occluding member is allowed to escape from the laterally-expanding occluding member during expansion of the radially-expanding structural member.

13. The device to occlude the aneurysm of claim 1, wherein the radially-expanding structural member is a stent.

14. The device to occlude the aneurysm of claim 1, wherein the radially-expanding structural member is expanded by a balloon.

15. The device to occlude the aneurysm of claim 1, wherein the radially-expanding structural member has sufficient structural strength to hold the laterally-expanding occluding member such that the laterally-expanding occluding member is configured to be against the aneurysm neck to occlude the aneurysm neck, but is sufficiently porous to allow blood flow to vessels branching from the parent vessel whose entrances from the parent vessel are configured to be covered by the radially-expanding structural member.

16. The device to occlude the aneurysm of claim 1, wherein the laterally-expanding occluding member and the radially-expanding structural member are configured to be inserted separately into the parent vessel.

17. The device to occlude the aneurysm of claim 1, wherein the laterally-expanding occluding member and the radially-expanding structural member are configured to be inserted together into the parent vessel.

18. The device to occlude the aneurysm of claim 1, wherein one or both of the laterally-expanding occluding member and the radially-expanding structural member are made of materials that are different in appearance from surrounding tissue in medical imaging.

19. A device to occlude an aneurysm comprising:
a laterally-expanding occluding member that is configured to be positioned within a parent vessel of the aneurysm and then expanded laterally;
wherein the lateral expansion is primarily in directions that are configured to be parallel to a plane defined by a circumference of an aneurysm neck; and
wherein the laterally expanding occluding member is expanded from a first configuration with a first width to a second configuration with a second width, wherein the second width is wider than the first width; and
a radially-expanding structural member that is configured to be positioned within the parent vessel of the aneurysm and then expanded radially after expansion of the laterally-expanding occluding member;
wherein the radially-expanding structural member is configured to span a section of the parent vessel that includes the aneurysm neck;
wherein the radially-expanding structural member is expanded from a first configuration with a first diameter to a second configuration with a second diameter, wherein the second diameter is larger than the first diameter;
wherein the radially-expanding structural member is structurally resilient to maintain the second configuration after expansion while the radially-expanding structural member is configured to be within the parent vessel;
wherein the radially-expanding structural member is positioned on the side of the laterally-expanding occluding member that is configured to face away from the aneurysm neck, such that the laterally-expanding occluding member is configured to be between the radially-expanding structural member and the aneurysm neck;
wherein expansion of the radially-expanding structural member presses and holds the laterally-expanding occluding member such that the laterally-expanding occluding member is configured to be in direct contact with the aneurysm neck, so that the laterally-expanding occluding member is configured to be at least partially covering the aneurysm neck and reduces blood flow to the aneurysm; and
wherein the laterally-expanding occluding member is substantially flat after expansion of the radially-expanding structural member.

* * * * *